United States Patent
Eggli et al.

(10) Patent No.: US 11,344,420 B2
(45) Date of Patent: May 31, 2022

(54) MODULAR KNEE PROSTHESIS

(71) Applicant: Stefan Eggli, Pierrafortscha (CH)

(72) Inventors: Stefan Eggli, Pierrafortscha (CH); Janosch Häberli, Bern (CH); Tom Overes, Langendorf (CH)

(73) Assignee: Stefan Eggli, Pierrafortscha (CH)

( * ) Notice: Subject to any disclaimer, the term of this patent is extended or adjusted under 35 U.S.C. 154(b) by 0 days.

(21) Appl. No.: 16/619,065

(22) PCT Filed: May 31, 2018

(86) PCT No.: PCT/IB2018/053885
§ 371 (c)(1),
(2) Date: Dec. 3, 2019

(87) PCT Pub. No.: WO2018/224924
PCT Pub. Date: Dec. 13, 2018

(65) Prior Publication Data
US 2020/0093604 A1    Mar. 26, 2020

(30) Foreign Application Priority Data
Jun. 4, 2017 (CH) .......................... 719/17

(51) Int. Cl.
*A61F 2/38*      (2006.01)
*A61F 2/30*      (2006.01)

(52) U.S. Cl.
CPC .......... *A61F 2/3859* (2013.01); *A61F 2/3877* (2013.01); *A61F 2002/30604* (2013.01);
(Continued)

(58) Field of Classification Search
CPC ........ A61F 2/3859; A61F 2/4684; A61F 2/38; A61F 2/3886; A61F 2002/4018;
(Continued)

(56) References Cited

U.S. PATENT DOCUMENTS 5,100,409 A * 3/1992 Coates ............... A61B 17/1764
606/88
6,749,638 B1 * 6/2004 Saladino ............... A61F 2/3859
623/20.14
(Continued)

FOREIGN PATENT DOCUMENTS

CN    201005807 Y    1/2008
CN    101426453 A    5/2009
(Continued)

OTHER PUBLICATIONS

CN Office Action in Application No. 201880036697.4 dated May 24, 2021.
(Continued)

*Primary Examiner* — Ann Schillinger
(74) *Attorney, Agent, or Firm* — Maschoff Brennan (57) ABSTRACT

The present invention relates to a modular knee prosthesis assembly kit for replacement of resected articular surfaces of a distal femur of a first patient side. The kit comprises at least one bi-condylar component sized and shaped to substantially replace resected posterior and distal condylar bone portions; and at least a first trochlear groove component and a second trochlear groove component, each sized and shaped to replace a resected trochlear groove bone portion. The first trochlear groove component comprises a first patella articulation path defining a first trochlear groove direction angle. The second trochlear groove component comprises a second patella articulation path defining a second trochlear groove direction angle. An assembly of the bi-condylar component and one of the first and second trochlear groove components forms a substantially complete femoral knee prosthesis. The second trochlear groove direction angle is different from the first trochlear groove direction angle.

17 Claims, 6 Drawing Sheets

(52) U.S. Cl.
CPC .............. *A61F 2310/00017* (2013.01); *A61F 2310/00029* (2013.01); *A61F 2310/00179* (2013.01)

(58) Field of Classification Search
CPC .... A61F 2002/30604; A61F 2002/3863; A61F 2002/3895; A61F 2002/4633; A61F 2002/30329; A61F 2/30734; A61F 2/461; A61F 2002/30607; A61F 2002/30616; A61F 2002/305; A61F 2002/30538; A61F 5/0123; A61F 2/3877; A61F 2310/00017; A61F 2310/00029; A61F 2310/00179
See application file for complete search history.

(56) References Cited

U.S. PATENT DOCUMENTS

| | | | |
|---|---|---|---|
| 2002/0138150 A1* | 9/2002 | Leclercq | A61F 2/3859 623/20.35 |
| 2003/0158606 A1* | 8/2003 | Coon | A61F 2/4637 623/20.15 |
| 2003/0220697 A1* | 11/2003 | Justin | A61F 2/3859 623/20.15 |
| 2004/0102852 A1 | 5/2004 | Johnson et al. | |
| 2006/0009774 A1 | 1/2006 | Dever et al. | |
| 2007/0100460 A1 | 5/2007 | Rhodes | |
| 2007/0173858 A1* | 7/2007 | Engh | A61F 2/461 606/99 |
| 2007/0219639 A1 | 9/2007 | Otto et al. | |
| 2011/0093081 A1* | 4/2011 | Chana | A61B 17/157 623/20.14 |
| 2011/0218635 A1 | 9/2011 | Amis et al. | |
| 2012/0083893 A1 | 4/2012 | Coon et al. | |
| 2012/0323334 A1 | 12/2012 | Jones et al. | |
| 2013/0226305 A1 | 8/2013 | Donno et al. | |
| 2014/0142713 A1* | 5/2014 | Wright | A61F 2/3859 623/20.21 |
| 2015/0164647 A1 | 6/2015 | Wellings et al. | |
| 2015/0216669 A1 | 8/2015 | Pierce | |
| 2016/0242919 A1 | 8/2016 | Engh et al. | |

FOREIGN PATENT DOCUMENTS

| | | | |
|---|---|---|---|
| CN | 102159158 A | 8/2011 | |
| CN | 103118633 A | 5/2013 | |
| EP | 0567705 A1 | 11/1993 | |
| EP | 1550419 A2 | 7/2005 | |
| EP | 2359775 A1 | 8/2011 | |
| EP | 2588032 A1 | 5/2013 | |
| EP | 3069693 A1 | 9/2016 | |
| JP | 2009-502235 A | 1/2009 | |
| WO | WO-9913803 A2 * | 3/1999 | .......... A61F 2/3859 |
| WO | 2007013959 A2 | 2/2007 | |
| WO | 2009029631 A1 | 3/2009 | |
| WO | 2009029631 A1 | 5/2009 | |

OTHER PUBLICATIONS

Swiss Research Report dated Aug. 29, 2017 for Swiss patent application No. CH00719/17 filed Jun. 4, 2017.

JP Office Action in Application No. 2020-516969 dated Mar. 29, 2022.

* cited by examiner

MODULAR KNEE PROSTHESIS

TECHNICAL FIELD OF THE INVENTION

The present invention relates to a total modular knee prosthesis assembly kit, and in particular to a kit which may be used to obtain a knee prosthesis with an exchangeable and individualised trochlear groove component.

BACKGROUND OF THE INVENTION

When the cartilage of the human knee is worn out due to trauma, wear or disease, the femoral bone and tibial bone cause pain to a person. This pain may be caused by the bone portions in the joint not being protected by cartilage, or inflammation of the soft tissue structures due to instability. People having worn out knees often undergo partial or total knee replacement to re-establish the function of the knee and to eliminate the pain.

A human knee joint consists of the distal femur, the proximal tibia, and the patella. The distal femur comprises a medial and lateral condyle, which articulate against the tibia plateau and form the tibia-femoral joint. Furthermore, the distal femur comprises a trochlear groove, located between and at least partly above the medial and lateral condyle, and which forms the articulation partner of the patella bone (knee cap), and which together form the patella-femoral joint. The knee is a modified hinge joint, allowing flexion and extension, as well as internal and external rotation.

The patella functions as a bony link between the major femoral extension muscles and the tibia. When the knee is extended from full flexion to full extension, the patella translates within the trochlear groove from the distal femur condyles to the anterior side. Due to its thickness, the patella increases the leverage arm of the muscles, and thus the efficiency of the upper leg muscles to move and stabilise the lower leg during the extension movement.

During a total knee replacement, the cartilage covered areas of the femur and tibia are removed and replaced by implant components, ideally acting as a natural healthy knee after surgery. A typical knee prosthesis consists of a monobloc metal femoral component, a metal tibial component and a polyethylene meniscal bearing between these, and optionally a polyethylene patella resurfacing component. Most often with straight cuts, the proximal end of the tibia is removed, the distal, anterior and posterior end of the femur are removed, followed by chamfer cuts.

Crucial for the long-term success of an artificial knee is a correct balance between the medial and lateral condyle, as well as a correct balance in flexion and extension. If one of the condyles receives more load than the other, this could cause excessive wear of a prosthesis and drastically reduce its lifespan. Furthermore, a too tight knee in extension, could limit straightening of the joint, whereas a too loose overall balance could make the knee to be unstable.

Thus, to reach a good outcome of a total or partial knee replacement, the functionality of the tibiofemoral joint is considered of great significance. This includes e.g. the relation between the extension and flexion gap, as well as the tension between the medial and lateral side within the knee. If an incorrect balance between flexion and extension on one hand, and the medial and lateral side on the other hand is observed, the surgeon can correct this by extra bone removal or selective ligament release. Ideally, in a frontal view, the tibia cut and the femoral cuts are oriented substantially parallel, and the medial and lateral side are in a correct balance.

The flexion and extension gap balancing not only defines the tibiofemoral joint, the major articulating elements of the knee, but may also have an influence on the patellofemoral joint. For example, any internal or external rotation in flexion may cause the patella groove to tilt, and therefore to become more or less prominent.

Any varus/valgus adaptation in extension may cause the patella groove to become more or less steep, and therefore forcing the patella in an unnatural direction.

Therefore, it is important to evaluate the patella tracking in the trochlear groove of the femoral component. A patellofemoral maltracking in a non-natural direction could cause the patella to undergo excessive loads. This may create painful stresses in the surrounding soft tissue (muscles, ligaments, tendons) or may even cause the patella to painfully luxate out of the trochlear groove. Also, due to the monobloc character of the knee implant components, which mostly are based on the average human anatomy, often compromises need to be made in the implant design. A correctly fitting tibiofemoral joint may come with a maltracking patellofemoral joint for many patients. This may also happen simply due to the fact that many anatomies show a natural trochlear groove angle, which strongly differs from the average human anatomy; the design base for the implant components. Thereby the rotation of the femoral component is strictly given by the tension of the collateral ligaments. Any loose situation on the medial side will turn the femoral component into an internal rotation, which will orientate the trochlea medially and therefore could lead to a lateralisation and thus to a maltracking of the patella. Concluding, a major disadvantage of monobloc knee femoral components is that the implant has a set relation between the shape and orientation of the condyles and the shape and orientation of the trochlear groove. A given rotation of the femoral component in flexion defines the orientation of the trochlea and therefore, any maltracking of the patella is practically unchangeable.

SUMMARY OF THE INVENTION

To provide an optimal post-operative functionality of a prosthetic knee and herewith patient satisfaction, a knee prosthesis system is required that can better adapt or individualise the patella tracking to the patient specific anatomy. Thus, it is the object of the present invention to overcome at least some of the problems identified above related to knee implants.

According to a first aspect of the invention, there is provided a modular knee prosthesis assembly kit as recited in claim 1.

The proposed new modular knee prosthesis assembly has the advantage that it allows a practitioner to obtain a total knee implant providing an interchangeable trochlear groove component to intraoperatively evaluate the patella tracking and providing the possibility to optimally set the implant trochlear groove orientation to the evaluated natural patella tracking orientation.

According to a second aspect of the invention, there is provided a method of preparing a modular knee prosthesis as recited in claim 16.

Other aspects of the invention are recited in the dependent claims attached hereto.

BRIEF DESCRIPTION OF THE DRAWINGS

Other features and advantages of the invention will become apparent from the following description of a nonlimiting example embodiment, with reference to the appended drawings, in which.

DETAILED DESCRIPTION OF THE INVENTION

Figure 1A:
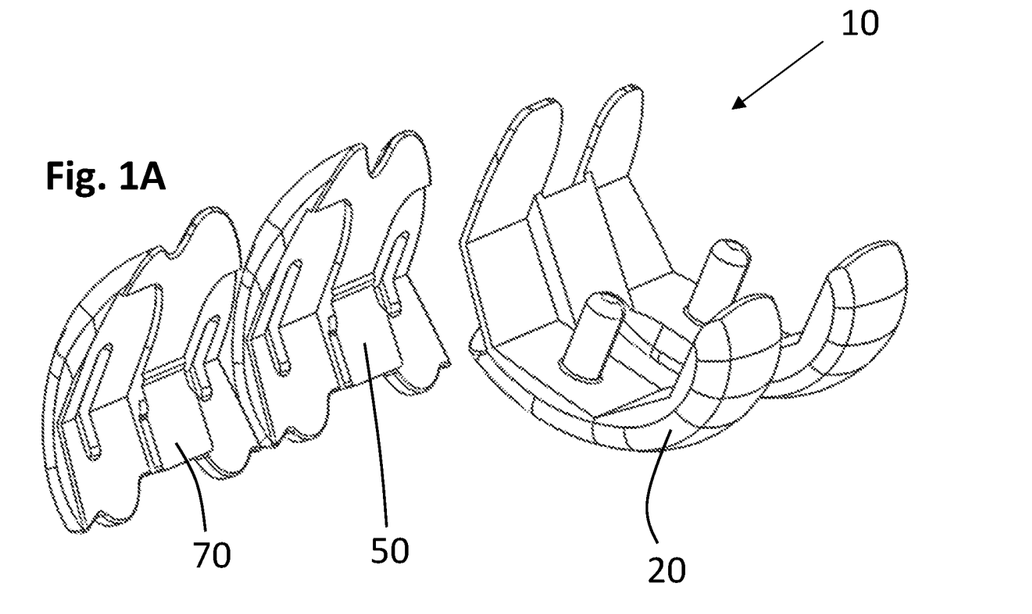
FIGS. 1A and 1B are perspective views illustrating an example modular knee prosthesis assembly kit according to the present invention.
Figure 1B:
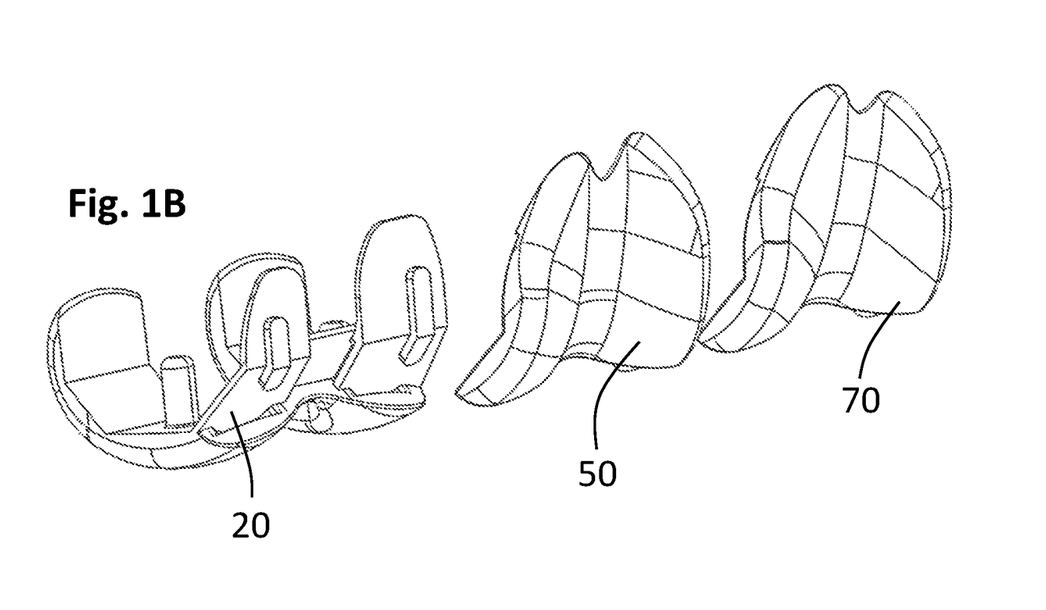

Referring to FIG. 1A, a modular total knee prosthesis assembly kit 10 for the replacement of the resected articular surfaces of a distal femur is shown. FIG. 1B depicts a bi-condylar component 20 and a first trochlear groove component 50 and a second trochlear groove component 70, anatomically shaped for the replacement of the right knee of a patient. A mirror image of the components would represent an example design for the left knee of the patient. FIG. 1B shows the same components as FIG. 1A but from a different angle. It is to be noted that the knee prosthesis assembly kit 10 may comprise further bi-condylar components 20 and/or trochlear groove components 50; 70, all designed for the same side of the patient (left or right side) and whose design is slightly different from each other as explained later in more detail. In the present example, the trochlear groove components 50; 70 and the bi-condylar component 20 are all monobloc components (i.e. constructed from a single piece). When assembled together, the bi-condylar component 20 and one of the trochlear groove components 50, 70 form a (modular) femoral component. In this example, the assembled femoral component is thus a two-piece component. The fact that the femoral component in this example consists of only two components (possibly in addition to some fastening elements, such as crews) has the advantage that the design can be kept simple.

Figure 2A:
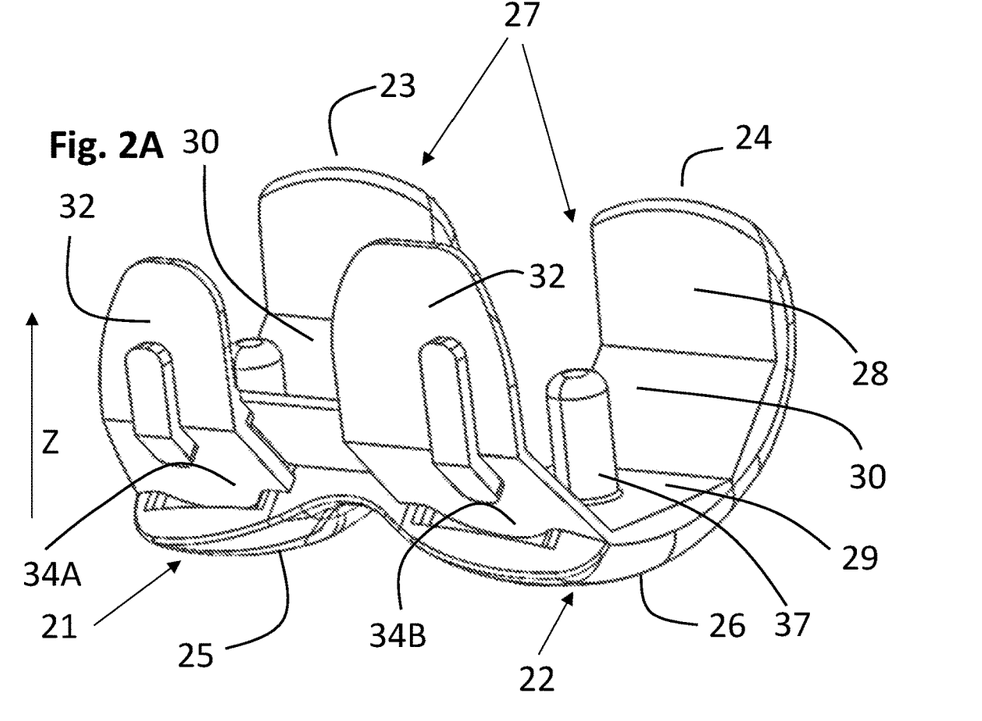
FIGS. 2A and 2B are perspective views illustrating in more detail an example bi-condylar component shown in FIG. 1.
Figure 2B:
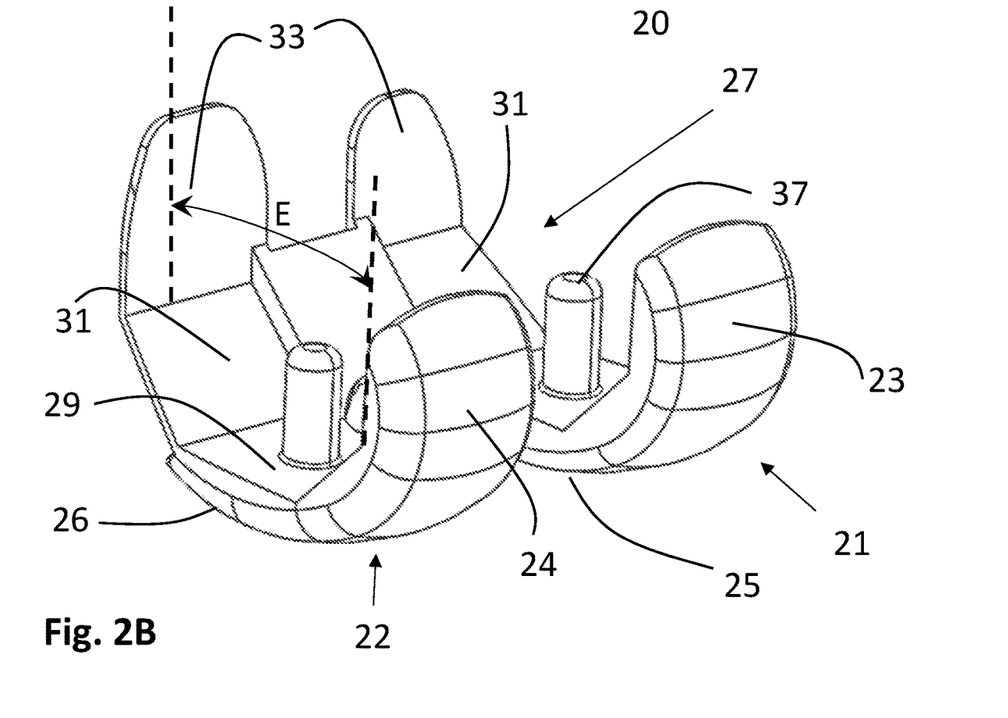

Referring to FIGS. 2A and 2B, the bi-condylar component 20 is shown in more detail. The bi-condylar component 20 is sized and shaped to replace the resected posterior and distal condylar bone portions. The bi-condylar component comprises a medial condyle 21 and a lateral condyle 22. Both condyles 21; 22, respectively comprise a posterior condyle portion 23; 24 and a distal condyle portion 25; 26. When the knee is in flexion (knee in bent position), the posterior condyle portions 23; 24 are engaged with the proximal tibia, and during the motion towards extension, the distal condyle portions 25, 26 engage with the proximal tibia. The medial and lateral condyles 21; 22 are intended to replace the articulating surfaces of the tibiofemoral joint of the knee.

The bi-condylar component 20 also comprises an inner box 27 (a non-closed box) or inner opening or inner space, comprising a posterior inner surface 28, a distal inner surface 29, a posterior inner chamfer surface 30 and an anterior inner chamfer surface 31. The chamfer surface is here understood to refer to a surface angled more than 90 degrees with respect to the plane defined by the posterior inner surface 28 or the distal inner surface 29. The inner box 27 is sized and shaped to engage or to become in contact with the resected distal femur. The inner surfaces may comprise bone cement pockets or comprise any structure providing means for osteointegration.

In this example, the bi-condylar component 20 comprises at least one supporting anterior strut (element) 32 or supporting, stabilising or protruding anterior element extending from the at least one distal condyle portion 25; 26 in a proximal direction Z. The proximal direction Z is indicated in FIG. 2A with an arrow. The anterior strut element 32 is sized and shaped to engage with the back sides 52; 72 (facing the femoral bone) of the trochlear groove components 50; 70 and forms a support to increase the mechanical stability of the trochlear groove components 50; 70. In this example, the anterior strut element 32 has an anterior inner surface 33 intended for direct engagement with the anterior resected target bone. Furthermore, in this example, the anterior inner surface 33 and the posterior inner surface 28 are oriented at an acute angle E between zero and ten degrees in a diverging manner. According to a variant of the present invention, the angle E is negative, and the posterior and anterior inner surfaces are oriented in a converging manner. The elasticity of the anterior strut element 32 can provide a press fit to the bone by either a wedging effect or an elastic press fit effect, or a combination thereof. It is further to be noted that the inner box 27 is in this example limited by the posterior inner surface 28, distal inner surface 29, posterior inner chamfer surface 30, anterior inner chamfer surface 31 and strut element 32. Thus, according to this example, no further surfaces limit the inner box 27. The bio-condylar component 20 further comprises a peg 37 for fixing the bi-condylar component 20 to the femoral bone.

Figures 3A, 3B, 3C:
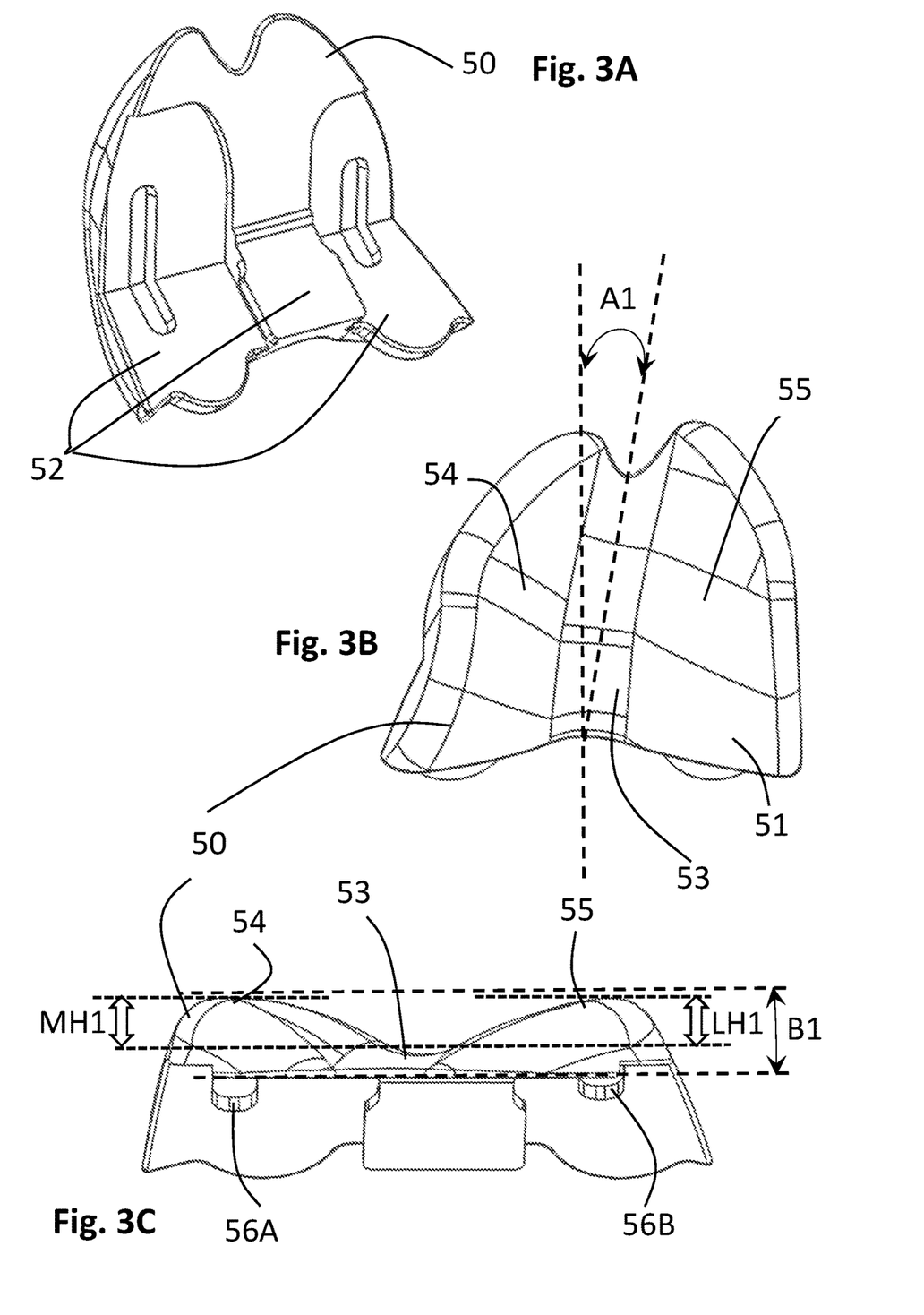
FIGS. 3A to 3C illustrate in more detail an example trochlear groove component shown in FIGS. 1A and 1B.

FIGS. 3A to 3C illustrate one example of the first trochlear groove component 50. The first trochlear groove component 50 comprises a first anterior articulation face 51, and a first back side face 52. The first articulation face 51 comprises a first patella articulation path 53, defining a first trochlear groove direction angle A1 and a first trochlear groove tilt angle B1. As depicted in FIG. 3B, the first trochlear groove direction angle A1 represents a direction of the trochlear path in the frontal plane, or how much the first patella articulation path deviates from a patella articulation path running straight and non-angled, i.e. a virtual line or plane parallel to the sagittal plane, whereas the first trochlear groove tilt angle B1 is projected in the transversal plane. The trochlear groove direction angle is thus an angle between a virtual line parallel to the sagittal plane and a line following the direction of the patella articulation path. The first trochlear groove tilt angle B1 is the angle between a substantially horizontal virtual line (when the first trochlear groove component 50 is placed onto a substantially horizontal surface) and a virtual line connecting a first medial top side or peak 54 and a first lateral top side or peak 55 of the first patella articulation path 53. In one example, the trochlear groove, forming the patella articulation path, has a substantially concave cross section having a depth, where the depth is defined by a substantially convex first medial peak or crest with a first medial height MH1 and a substantially convex first lateral peak or crest with a first lateral height LH1. More specifically, the depth is defined between the height difference between the bottom of the groove and any one of the lateral or medial peaks. The trochlear groove has a shape of a wave form, and the depth may or may not be constant along the trochlear groove. In this example, the width in the medial-lateral direction of the trochlear groove component substantially equals the width of the bi-condylar component. Thus, in this example, the trochlear groove component comprises the patella articulation path and the medial and lateral peaks. In one example, the first medial height MH1 and the first lateral height LH1 are substantially the same or similar to each other as shown in FIG. 3C. In another example, the heights are substantially different. To summarise, the first trochlear groove direction angle A1 defines the tracking or translation direction of the patella, i.e. the orientation of the first patella articulation path, whereas the medial and lateral peaks define the height of the groove walls of the first articulation path, which prevent the patella from leaving the groove.

The first trochlear groove component 50 is sized and shaped to replace the resected anterior area of the distal femoral bone. Furthermore, the first trochlear groove component 50 is sized and shaped to engage substantially seamlessly with said bi-condylar component 20. For assembly stability, the trochlear groove component 50, 70 may comprise one or more wings 56A, 56B configured for engaging with one or more complementary shaped pockets or recesses 34A, 34B (see FIG. 2A) in the bi-condylar component 20. The wings and pockets may aid assembly steps, as well as provide stabilisation. Alternatively, the bi-condylar component 20 may comprise one or more wings for engaging with one or more pockets in the trochlear groove component 50, 70.

Figure 4A:
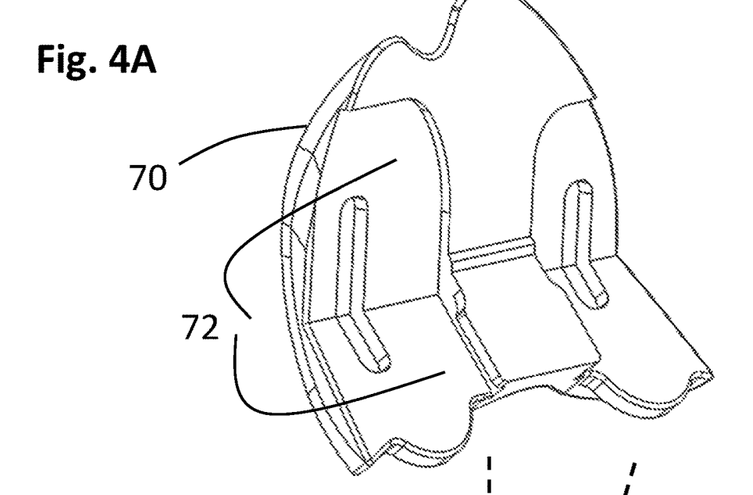
FIGS. 4A to 4C illustrate in more detail another example of a trochlear groove component shown in FIGS. 1A and 1B.
Figure 4B:
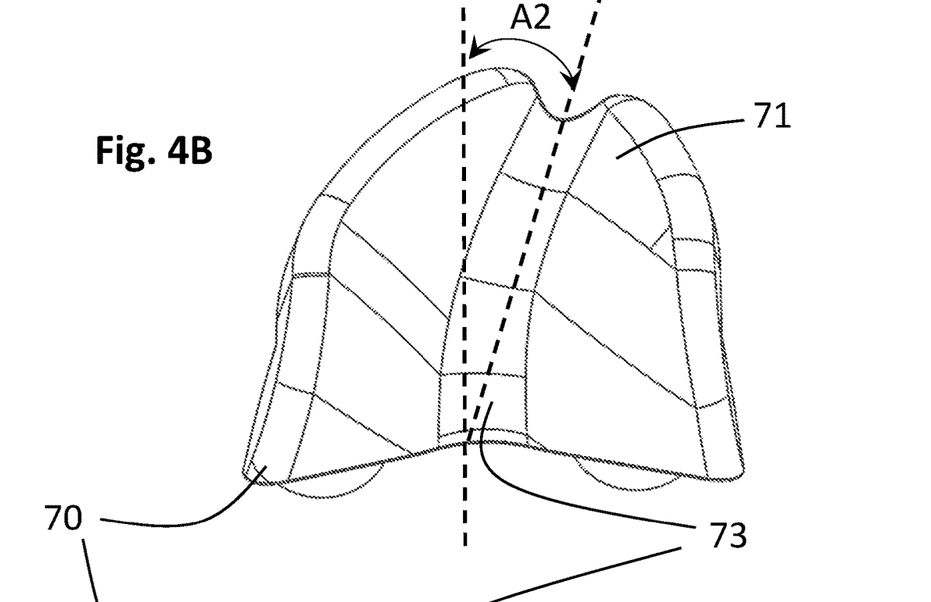
Figure 4C:
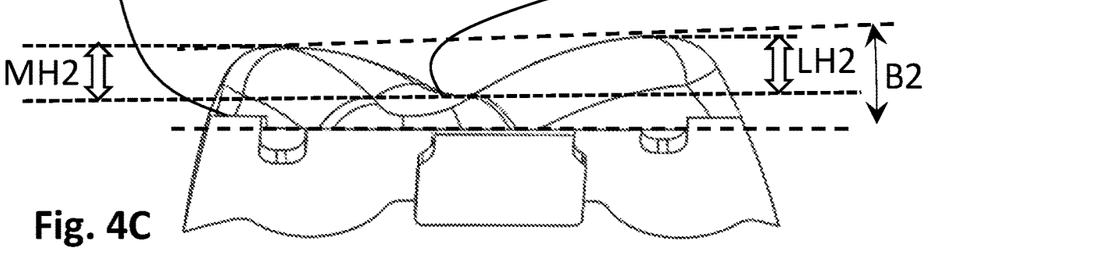

Referring to FIGS. 4A to 4C, an example of the second trochlear component 70 is shown. The second trochlear groove component 70 comprises a second anterior articulation face 71 and a second back side face 72. The second articulation face 71 comprises a second patella articulation path 73, defining a second trochlear groove direction angle A2 and a second trochlear groove tilt angle B2. As depicted, the first and second trochlear groove components 50; 70 are substantially similar in shape, except for at least one of the trochlear groove direction angle and trochlear groove tilt angle. FIG. 4C also shows a second medial height MH2 and a second lateral height LH2. These heights are however not explained here in more detail because the above explanations of MH1 and LH1 also apply here.

According to one example, the first and second trochlear groove direction angles A1; A2 of the first and second trochlear groove components 50; 70, respectively, are not the same. The first and second trochlear groove direction angles A1; A2 may differ by at least 3° or more specifically by at least 5° or 7°. In other words, the first and second patella articulation paths 53; 73 would be oriented in different directions. Furthermore, in addition to, or instead of the different first and second trochlear groove direction angles A1; A2, the first and second trochlear groove tilt angles B1; B2 may not be the same. The first and second trochlear groove tilt angles B1; B2 may differ by at least 1° or more specifically by at least 3°, 5° or 7°.

During the surgical knee replacement procedure, the proximal end of the tibia is removed, the distal, anterior and posterior end of the femur is removed, followed by chamfer cuts. Advantageously, before removal of the anterior end of the femoral bone, the orientation and tilt of the trochlear groove is analysed. Now, based on the established trochlear groove orientation and tilt, the best matching trochlear groove component 50; 70 out of the modular total knee prosthesis assembly kit 10 is selected and rigidly fixated to said bi-condylar component 20. Herewith the knee prosthesis is adapted or individualised to the patella tracking of the patient specific anatomy.

Therefore, the surgical method of defining and preparing a total or complete femoral knee prosthesis comprising a bi-condylar component 20 and a trochlear groove component 50; 70 thus comprises at least some of the following steps:

defining the femoral component anterior to posterior size and related medial to lateral size, establishing a spatial relationship between anatomical references, such as the intramedullary axis of the knee, and the trochlear groove direction, referencing and/or defining the anatomical trochlear groove direction, establishing a spatial relationship between anatomical references, such as the epicondylar axis and/or posterior condyles of the knee, and the trochlear groove tilt, referencing and/or defining the anatomical trochlear groove tilt, selecting the appropriate bi-condylar component out of a set of bi-condylar components, selecting the appropriate trochlear groove component out of a set of trochlear groove components for the selected (given) bi-condylar component, engaging the selected trochlear groove component with the selected bi-condylar component, optionally adding at least one fixation means (not shown), such as at least one screw, bolt, snapping element and/or glue, for connecting the bi-condylar component 20 and the trochlear groove component together. In addition to, or instead of any of the above fixation means, the connection between the bi-condylar component and the trochlear groove component may be a press-fit connection.

Figure 5A:
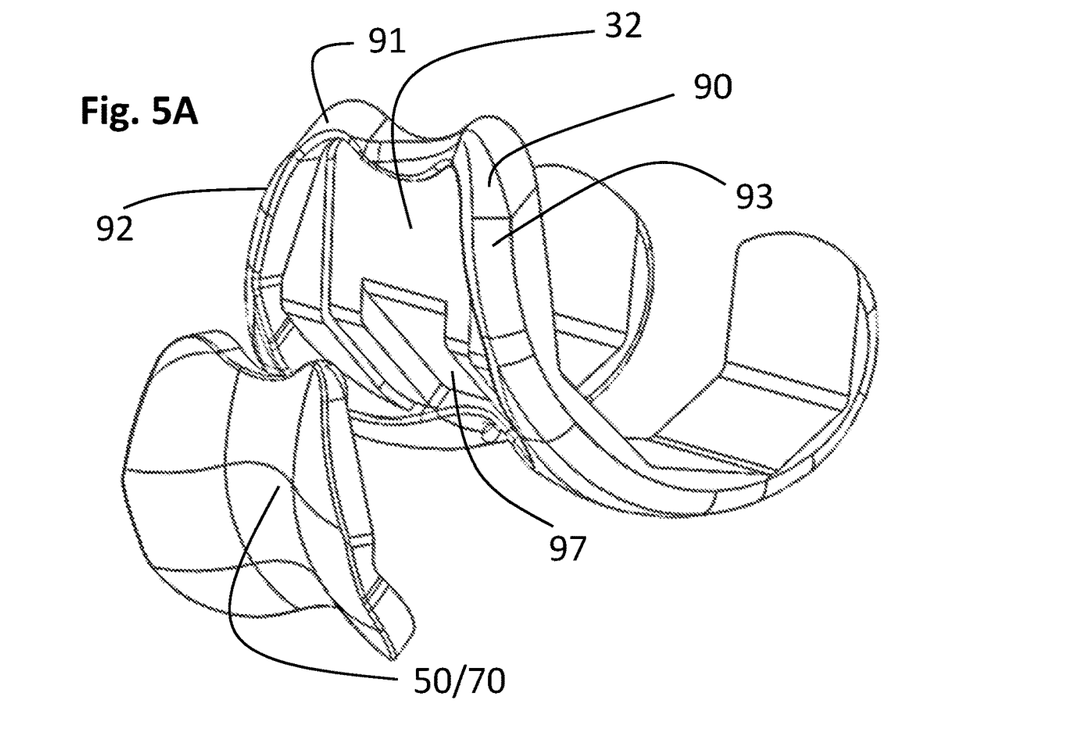
FIGS. 5A and 5B are perspective views illustrating an example bi-condylar component according to a variant of the present invention.
Figure 5B:
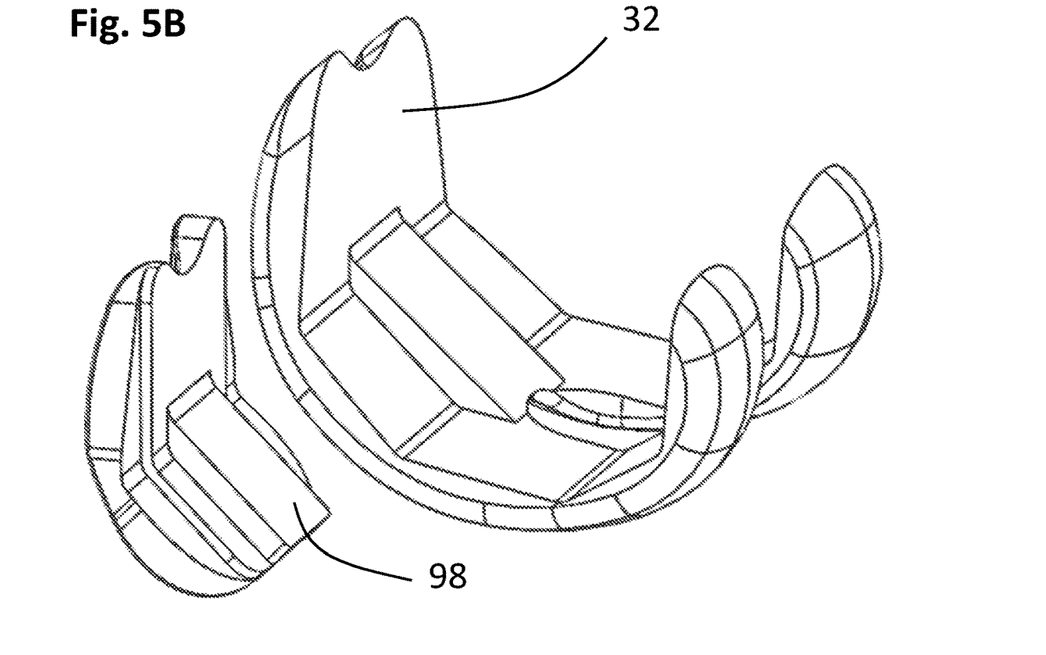

Referring to FIGS. 5A and 5B, an alternative design is shown for the bi-condylar component 20 and for the first or second trochlear groove components 50; 70. More specifically, in the design of FIGS. 5A and 5B, the anterior strut 32 has a different shape and structure compared to the anterior strut 32 shown e.g. in FIGS. 2A and 2B. The bi-condylar component 20 of FIGS. 5A and 5B comprises a supporting anterior strut 32 comprising a peripheral and protruding rim 90 for capturing the trochlear groove component 50; 70 from at least one of a proximal side 91, medial side 92 and a lateral side 93 in a recess or pocket formed in the bi-condylar component 20. The rim 90 has an increased thickness, and therefore increases the mechanical stability. In the illustrated example, the peripheral rim substantially surrounds the trochlear groove component 50; 70. The trochlear groove component can thus be considered to be an insert, which is partially or fully received by the bi-condylar component 20. The rim 90 may protrude the same amount from the surface of the anterior strut 32 as is the cross-sectional thickness of the trochlear groove component 50; 70. In this manner, when the trochlear groove component 50; 70 is assembled with the bi-condylar component 20, the trochlear groove component 50; 70 may substantially not protrude from the surface of the bi-condylar component 20 and forms a (substantially smooth) surface flush with the bi-condylar component 20. The bi-condylar component 20 in this example further comprises guiding means 97, such as a guiding slot, to receive a guiding protrusion 98 of the trochlear groove component 50; 70. It is to be noted that a similar guiding arrangement is also provided in the design shown e.g. in FIGS. 1A and 1B. The guiding arrangement also improves the stability of the assembled prosthesis (when the trochlear groove component 50; 70 is engaged with the bi-condylar component 20).

Figure 6:
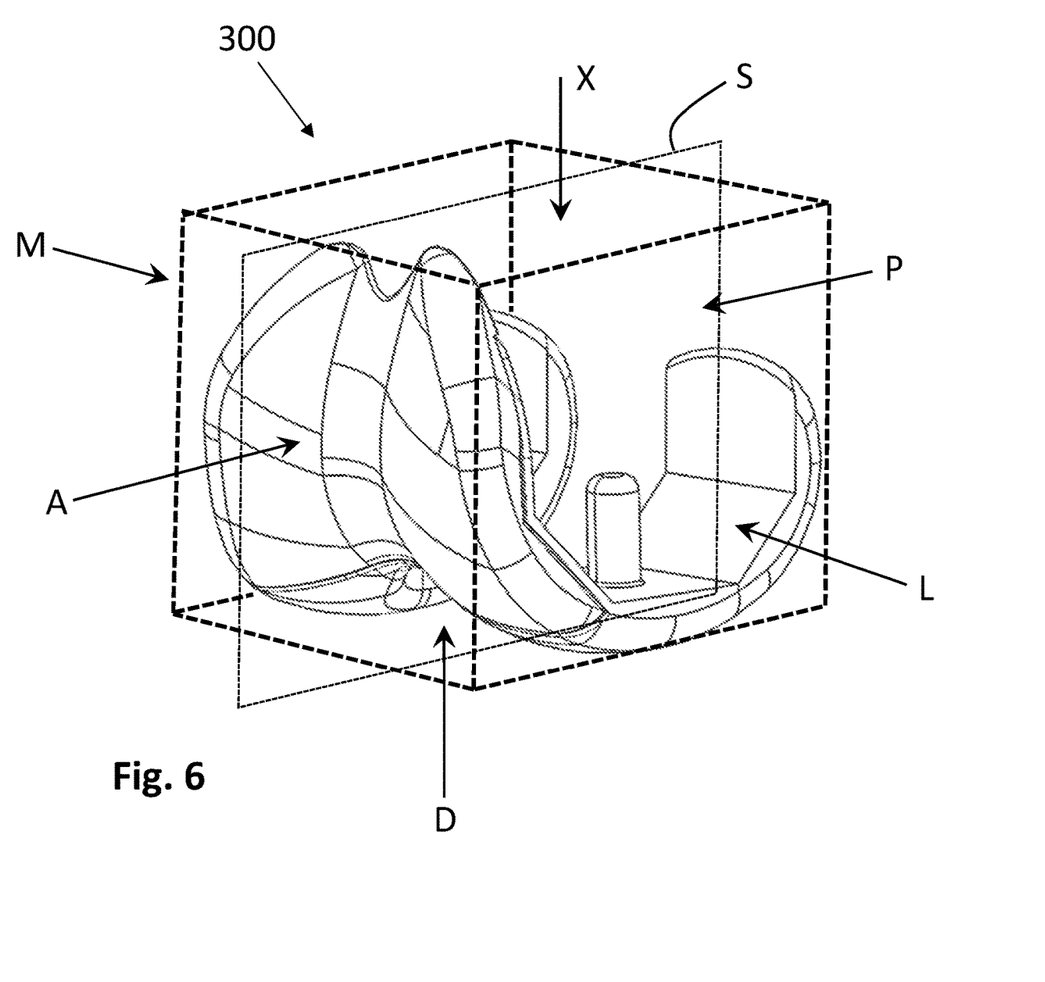
FIG. 6 is a perspective view showing an assembled modular knee prosthesis together with multiple virtual planes and view directions.

Referring to FIG. 6, the assembled total modular knee prosthesis 300 including multiple virtual planes and view directions is shown in a perspective view. The virtual planes elucidate the anatomical view directions and sides of the knee prosthesis in accordance with anatomical view directions and planes of the human body, as being described in the present description. A view direction is oriented substantially perpendicular to the respective virtual plane.

Plane A is the anterior plane, which coincides with the anterior or front side of the prosthesis.

Plane P is the posterior plane, which coincides with the posterior or rear side of the prosthesis.

Plane D is the distal plane, which coincides with the distal end or side of the prosthesis.

Plane X is the proximal plane, which coincides with the proximal end or side of the prosthesis.

Plane M is the medial plane, which coincides with the medial side of the prosthesis.

Plane L is the lateral plane, which coincides with the lateral side of the prosthesis Plane S is the sagittal plane, which is the virtual plane through the prosthesis centre, substantially perpendicular to the medial and lateral plane.

Most common total knee prostheses are made of biocompatible materials, such as cobalt chromium steel or titanium (alloys) or ceramic materials. According to the present invention, the trochlear groove components 50; 70 may be made of any biocompatible plastic, such as polyethylene, polyetheretherketon, polyoxymethylene, and/or polyphenylsulfone, whereas the bi-condylar component 20 may be made of any suitable biocompatible material, such as ceramic material and/or metal including e.g. cobalt-chrome and/or stainless steel. It is expected that polyethylene and polyetheretherketon have a lower friction coefficient against the articulating cartilage of the patella bone, and therefore can reduce wear. Furthermore, the loads on the trochlear groove components are considered marginal. The trochlear groove components may be manufactured by milling, additive manufacturing or injection moulding, or by any combination thereof. It is to be noted that the bi-condylar components 20 and/or the trochlear groove components 50; 70 may form a trial (temporary) knee prosthesis, but they may also form a long term implantable knee prosthesis implanted once the trial knee prosthesis has been removed.

While the invention has been illustrated and described in detail in the drawings and foregoing description, such illustration and description are to be considered illustrative or exemplary and not restrictive, the invention being not limited to the disclosed embodiment. Other embodiments and variants are understood, and can be achieved by those skilled in the art when carrying out the claimed invention, based on a study of the drawings, the disclosure and the appended claims.

In the claims, the word "comprising" does not exclude other elements or steps, and the indefinite article "a" or "an" does not exclude a plurality. The mere fact that different features are recited in mutually different dependent claims does not indicate that a combination of these features cannot be advantageously used.

The invention claimed is:

1. A modular knee prosthesis assembly kit for replacement of resected articular surfaces of a distal femur of a first patient side, the modular knee prosthesis assembly kit comprising:
   a) a single monobloc bi-condylar component sized and shaped to substantially replace resected posterior and distal condylar bone portions,
   b) a first trochlear groove component and a second trochlear groove component, each sized and shaped to replace a resected trochlear groove bone portion, the first trochlear groove component comprising a first patella articulation path defining a first trochlear groove direction angle, the second trochlear groove component comprising a second patella articulation path defining a second trochlear groove direction angle,
   wherein an assembly of the single monobloc bi-condylar component and one of the first and second trochlear groove components forms a substantially complete femoral knee prosthesis, wherein both the first and second trochlear groove components are sized and shaped to engage with the single monobloc bi-condylar component, and wherein the first trochlear groove direction angle is different from the second trochlear groove direction angle, and the first trochlear groove component and the second trochlear groove component are of the same size.

2. The modular knee prosthesis assembly kit according to claim 1, wherein the difference between the second trochlear groove direction angle and the first trochlear groove direction angle is at least 3 degrees.

3. The modular knee prosthesis assembly kit according to claim 1, wherein:
   the first patella articulation path has a concave cross section and is located between a first medial peak with a substantially convex cross section and with a first medial height, and a first lateral peak with a substantially convex cross section and with a first lateral height, and
   the second patella articulation path has a concave cross section and is located between a second medial peak with a substantially convex cross section and with a second medial height, and a second lateral peak with a substantially convex cross section and with a second lateral height.

4. The modular knee prosthesis assembly kit according to claim 3, wherein the first medial height, the second medial height, the first lateral height and the second lateral height are all substantially the same.

5. The modular knee prosthesis assembly kit according to claim 3, wherein the first medial height is different from the second medial height, and/or the first lateral height is different from the second lateral height.

6. The modular knee prosthesis assembly kit according to claim 1, wherein the assembly forms a trial knee prosthesis.

7. The modular knee prosthesis assembly kit according to claim 1, wherein the assembly forms a long term implantable knee prosthesis.

8. The modular knee prosthesis assembly kit according to claim 1, wherein the bi-condylar component comprises a supporting anterior strut element, sized and shaped to engage with a back side of any one of the first and second trochlear groove components to increase stability of the engaged trochlear groove component.

9. The modular knee prosthesis assembly kit according to claim 1, wherein the bi-condylar component comprises a supporting anterior strut element comprising a peripheral, protruding rim for capturing any one of the first and second trochlear groove components from at least one of proximal, medial and lateral side.

10. The modular knee prosthesis assembly kit according to claim 1, wherein the kit comprises fixation means for fixing any one of the first and second trochlear groove components to the bi-condylar component.

11. The modular knee prosthesis assembly kit according to claim 1, wherein any one of the first and second trochlear groove components is made of biocompatible plastic.

12. The modular knee prosthesis assembly kit according to claim 1, wherein the bi-condylar component is made of biocompatible material.

13. The modular knee prosthesis assembly kit according to claim 1, wherein the width in a medial-lateral direction of the first and/or second trochlear groove component(s) substantially equals the width of the bi-condylar component.

14. The modular knee prosthesis assembly kit according to claim 1, wherein the first and/or second trochlear groove component(s) comprise(s) at least one protruding engagement element for engaging with at least one pocket in the bi-condylar component, or wherein the first and/or second trochlea groove component(s) comprise(s) at least one pocket for engaging with at least one protruding engagement element in the bi-condylar component.

15. The modular knee prosthesis assembly kit according to claim 1, wherein the first and/or second trochlear groove component(s) further comprise(s) a first or second medial peak, respectively, and a first or second lateral peak, respectively, forming therebetween the first or second patella articulation path, respectively.

16. The modular knee prosthesis assembly kit according to claim 1, wherein any one of the first and second trochlear groove components is made of polyethylene, polyetheretherketon, polyoxymethylene, or polyphenylsulfone, or combinations thereof.

17. The modular knee prosthesis assembly kit according to claim 1, wherein the bi-condylar component is made of cobalt-chrome, stainless steel, or ceramic material, or combinations thereof.

* * * * *